United States Patent [19]

Chen et al.

[11] Patent Number: 5,593,853
[45] Date of Patent: Jan. 14, 1997

[54] GENERATION AND SCREENING OF SYNTHETIC DRUG LIBRARIES

[75] Inventors: Hao Chen, Adelphia; Richard Radmer, Baltimore, both of Md.

[73] Assignee: Martek Corporation, Columbia, Md.

[21] Appl. No.: 194,224

[22] Filed: Feb. 9, 1994

[51] Int. Cl.$^6$ .............................. C12Q 1/02; C12Q 1/00; C12Q 1/18
[52] U.S. Cl. ..................... 435/29; 435/4; 435/32; 536/1.11; 536/118; 536/123.1; 536/115
[58] Field of Search .................................. 435/29, 4, 25, 435/24, 6, 32; 536/115, 117, 118, 119, 123.1, 4, 1.11

[56] References Cited

U.S. PATENT DOCUMENTS

| | | | |
|---|---|---|---|
| 3,251,827 | 5/1966 | Schnell et al. | 536/119 |
| 3,859,318 | 1/1975 | Lesuer | 536/118 |
| 4,005,195 | 1/1977 | Jandacek | 424/125 |
| 4,241,054 | 12/1980 | Volpenhein et al. | 536/119 |
| 4,260,827 | 4/1981 | Klinkmann et al. | 536/119 |
| 4,631,211 | 12/1986 | Houghten | 428/35 |
| 4,833,092 | 5/1989 | Geysen | 436/501 |
| 5,223,409 | 6/1993 | Ladner et al. | 435/69.1 |

FOREIGN PATENT DOCUMENTS

| | | |
|---|---|---|
| 2640627 | 12/1988 | France . |
| WO92/00091 | 7/1991 | WIPO . |
| WO93/06121 | 9/1992 | WIPO . |
| WO94/19360 | 2/1994 | WIPO . |
| WO95/03315 | 7/1994 | WIPO . |

OTHER PUBLICATIONS

Nielsen, et al., "Synthetic Methods for the Implementation of Encoded Combinatorial Chemistry", *J. Am. Chem. Soc.*, 115:9812–9813 (1993).

Lowman, et al., "Selecting High–Affinity Binding Proteins by Monvalent Phage Display", *Biochemistry*, 30:10832–10838 (1991).

Amato, "Speeding Up a Chemical Game of Chance", *Science*, 257:330–331 (1992).

Brenner, et al., "Encoded Combinatorial Chemistry", *Proc. Natl. Acad. Sci. USA*, 89:5381–5383 (1992).

Ganellin, "Past Aproaches to Discovering New Drugs", *Medicinal Chemistry for the 21st Century*, Ed. by Wermuth, Koga, Konig, and Metcalf, Blackwell Scientific Publications, London, pp. 3–12, 1992.

Jung, et al., "Multiple Peptide Synthesis Methods and Their Applications", *Angewandt Chemie*, 31(4):367–383 (1992).

Bradley, "How to Create a Drug Library", *New Scientists*, Issue of Feb. 13, 1993.

Barry, et al., "Susceptibility Tests: Diffusion Test Procedures", 4th Edition of *Manual of Clinical Microbiology*, ed. by Lennette, American Society for Microbiology, Washington, D.C., pp. 978–987, 1985.

Glasr, "Peptide Synthesis and Screening Strategies for Drug Development", *Genetic Engineering News*, Issue of May 1, 1993.

Potera, "In Vitro Evolution Creates Novel Drugs", *Genetic Engineering News*, Issue of Apr. 15, 1993.

"IXSYS Licenses In Vitro Monoclonal Process", *Genetic Technology News*, 12(10):14, Oct. 1992.

"Progenics Improves the Screening Process", *Genetic Gechnology News*, 9(5):5, May 1989.

Baum, "Combinatorial Approaches Provide Fresh Leads for Medicinal Chemistry", C&EN, Feb. 7, 1994.

Stone, "The Hot New Field of Molecular Diversity", *Bio/Technology*, 11:1508–1509, Dec. 1993.

*Primary Examiner*—John Kight
*Assistant Examiner*—Louise N. Leary
*Attorney, Agent, or Firm*—Banner & Witcoff, Ltd.

[57] ABSTRACT

Methods are provided for generating highly diverse mixtures of compounds which may be screened for biological activities. Once the activity is found, the component of the mixture which is responsible for the activity can be isolated by fractionation and assay for the biological activity. Polyhydroxylated organic monomers and oligomers are used as starting materials for generating the libraries.

59 Claims, 3 Drawing Sheets

GENERATION AND SCREENING OF SYNTHETIC DRUG LIBRARIES

TECHNICAL FIELD OF THE INVENTION

This invention is concerned with generating libraries of compounds for the discovery of bioactive leads and novel chemical entities. The active leads generated and identified by this invention can be used for the development of pharmaceuticals, agrochemicals, and the like.

BACKGROUND OF THE INVENTION

Drug discovery processes are very lengthy. A conventional process involves testing and screening of thousands of individual compounds for a desired therapeutical activity. Historically, less than 1 in 10,000 of the synthetic compounds have made it to the drug market, at costs greater than $200 million per drug (Ganellin, C. R., 1992, in *Medicinal Chemistry for the 21st Century*, Ed. by Wermuth, C. G.; Koga, N.; Konig, H.; and Metcalf, B. W. Blackwell Scientific Publications, London; pp. 3–12).

Drugs have been sought from natural products for many years. Complex mixtures made from cells or their secondary metabolites have been screened for biological activity. When a desired biological activity has been found in such a complex mixture, the particular chemical which has the activity has been purified, using the biological activity as the means of identifying the component of the mixture which contains the desired activity.

An alternative method for screening compounds for desirable biological activities has been to screen individual compounds which have been synthesized and saved in libraries of drug or chemical companies or research institutes. The compounds in these libraries were often chosen for synthesis and screening because they had a particular functionality thought to be relevant to a particular biological activity.

More recently, some companies have begun to create their own peptide and oligonucleotide libraries to screen for a particular biological function. "Peptide Library Synthesis and Screening Strategies for Drug Development", *Genetic Engineering News*, May 1, 1993, page 6; "Ixsys Licenses In Vitro Monoclonal Process", *Genetic Technology News*, vol. 12, page 14, October 1992; and Ladner, U.S. Pat. No. 5,223,409; "In Vitro Evolution Creates Novel Drugs," *Genetic Engineering News*, page 1, Apr. 15, 1993. The combinatorial peptide and nucleotide libraries described to date involve the sequence randomization of individual monomers using a single naturally existing biological linkage (such as 3'–5' phosphate linkage of nucleotides or amide linkage of peptides).

J. H. Musser, "Trends in New Lead Identification" in *Medicinal Chemistry for the 21st Century*, edited by Wermuth, Koga, Konig and Metcalf, teaches that carbohydrates have the potential for greater complexity than polypeptides or oligonucleotides. He opines that "of all the structural types, carbohydrates have the greatest theoretical potential for specificity and new lead generation."

Carbohydrates are a large family of organic molecules with highly functionalized carbon skeletons. They share the structure $C_x(H_2O)_y$. In fact, this may be the only readily available family of molecules where almost every carbon within the skeleton is functionalized. These functionalizations and related stereochemical differences also result in different chemical reactivities for individual carbon atoms.

The great potential of carbohydrates for use in generating organic compound libraries rests within the inherent character of this class of compounds. Almost every carbon in a given carbohydrate has a hydroxyl functionality (or other oxygen-containing functional group) attached to it. Different spatial arrangements (stereochemical arrangements) of these hydroxyl groups result in different carbohydrates; for example, the difference between glucose and galactose is attributable to the stereochemistry of the hydroxyl group attached to the C-4 carbon. Different linkages between carbohydrates derived from these hydroxyl functionalities (i.e., by removal of a water molecule) also result in different carbohydrates. As a consequence, the potential number of different saccharides generated by combining several saccharities together can be very large.

When two hexoses are linked together via a glycosidic bond (a chemical linkage involving the anomeric carbon of at least one of the saccharides), eleven different disaccharides can theoretically be obtained. A mixture of three monosaccharides can, in theory, generate as many as 1056 possible trisaccharide combinations, and a mixture of five different monosaccharides can be assembled into 31 million pentasaccharides. In addition, if the reaction conditions produce sugar anhydride linkages, the combinatory possibilities increase many fold. For instance, two identical monosaccharides can generate a total number of 26 different dimers of sugar anhydrides and glycosides.

Recently, new screening processes have been developed which have the potential for high throughput, i.e., many compounds per unit time can be tested individually for a particular biological activity. See "Progenics Improves the Screening Process", *Genetic Technology News*, vol. 9, page 5, May 1989; "Nova gets $2.5 Million for AIDS", *Biotechnology Newswatch*, vol. 8, page 2, Dec. 19, 1988; "RT speeds screening for new drugs" *Chemical Week*, Apr. 15, 1987, page 19. Such screening techniques involve testing for inhibitors of specific proteins, or binding to particular cellular receptors. These screening processes are typically performed on pre-existing libraries of chemicals. See "Newsfront: Companies" *Chemical Engineering*, page 35, Sep. 16, 1985; and "RT speeds screening for new drugs" *Chemical Week*, Apr. 15, 1987, page 19.

The potential diversity of polyhydroxyl-containing organic compounds and the newly developed screening procedures, have together generated an opportunity for devising new methods to generate rapidly novel, large libraries of diverse chemicals for screening for bioactive compounds.

SUMMARY OF THE INVENTION

It is an object of the invention to provide methods for generating libraries of compounds.

It is another object of the invention to provide a method to rapidly produce large libraries of diverse compounds.

It is still another object of the invention to provide a synthetic strategy for the chemical preparation of a library of compounds based on polyhydroxyl-containing organic compounds.

It is yet another object of the invention to provide a library of compounds by means of chemical synthesis.

It is another object of the invention to provide a library of compounds for use in pharmaceutical and agrochemical screening and discovery.

It is still another object of the invention to generate compounds for therapeutic use.

These and other objects of the invention are provided by one or more of the embodiments described below. In one embodiment a method for generating and screening a library of compounds is provided which comprises:

reacting one or more polyhydroxyl-containing organic compounds with subequimolar amounts of displacing groups to form a first mixture comprising displacing group-substituted polyhydroxyl-containing organic compounds;

testing said first mixture or a reaction product made therefrom for the presence of a component having a biological activity.

According to a second embodiment of the invention a method is provided for generating and screening a library of compounds. The method comprises:

reacting one or more polyhydroxyl-containing organic compounds with subequimolar amounts of protecting groups to form a first mixture of randomly protected polyhydroxyl-containing organic compounds;

oxidizing said first mixture to form a second mixture comprising carbonyl-containing organic compounds;

testing said first or said second mixtures or a reaction product made therefrom for the presence of a component having a biological activity.

These and other embodiments of the invention, which are described in more detail below, provide the art with means of generating complex mixtures of compounds which may or may not exist in nature and of determining useful compounds among said complex mixtures.

DETAILED DESCRIPTION OF THE PREFERRED EMBODIMENTS

It is a discovery of the present invention that complex mixtures of polyhydroxyl compounds can be generated, transformed, and screened in large numbers by means of randomizing chemosynthetic strategies. Using such strategies, useful compounds have been synthesized and identified in pools of compounds.

The polyhydroxyl-containing organic compounds used in the present invention have at least two hydroxyl functionalities and contain a carbon—carbon backbone of at least two carbons atoms. The carbon—carbon backbone of the compounds may be saturated or unsaturated, cyclic or linear. The compounds include: carbohydrates, polyalcohols (e.g., ethylene glycol and glycerol) and polyphenols (e.g., hydroquinones and tetracyclines). Carbohydrate, saccharide, sugar and carbohydrate-transformed compounds are defined herein to include all chemical moieties having a saccharide unit or which are transformed from a saccharide. These terms may also include glycopeptides, glycolipids and other biopolymers (or biomacromolecules) containing saccharides, either in their entirety or as part of the molecular framework.

Carbohydrates, though promising as Musser pointed out, and discussed extensively herein for the purpose of demonstration, merely represent a portion of a much larger family of polyhydroxylated organic compounds useful for purposes of this invention. In addition to carbohydrates, polyhydroxylated organic compounds include: monomeric acyclic compounds, such as ethylene glycol, glycerol, and 1, 2, 3,-trihydroxy pentane; polymeric acyclic compounds, such as di- or tri-ethylene diglycol; monomeric cyclic compounds, such as inositol and 1,2,3-trihydroxycyclopentane; polymeric cyclic compounds, such as di-inositol; polymeric and monomeric unsaturated compounds such as tetrahydroxy-1,4-quinone hydrated and polyphenols, such as tetracyclines; and combinations thereof. For example a reaction between glycerol and glucose can produce twelve different isomers by glycosidic and anhydride linkages. A compound library may also be built via the chemical reactions of phenolics and polyphenolics and other polyoxygenated chemicals. For example, when glycerol is combined via an ether linkage with 2,4-dihydroxytoluene, four different isomers of the toluene-hydroxypropyl ether compounds are made.

Key to the achievement of randomization of reaction products is the use of subequimolar amounts of reactants, either displacing groups or protecting groups. Use of such amounts maximizes the number of different products which can be achieved. Equimolar amounts, according to the present invention, are assessed against the number of hydroxyl moieties which are available for reaction.

Displacing groups according to the present invention can be any which are known in the art to directly or indirectly displace a hydroxyl group from a carbon atom. These include halogen ions, azide ions, nitriles, sulfites, and alkoxides. Often it is desirable to activate the hydroxyl moieties prior to the step of displacement. Any suitable activation group can be used. Thus activation can be accomplished by reaction with a halide salt, such as bromine or iodine salt, or with methanesulfonyl chloride to yield a sulfonyl ester. Similarly, activation is desirable prior to oligomerizing polyhydroxyl compounds. Useful for such activation reactions are sulfonyl compounds, halide compounds, and thio-compounds.

The oligomerizing reactions of the present invention include, but are not limited to, (1) the formation of a glycosidic bond, (e.g., the elimination of a water molecule between the anomeric hydroxyl group of one sugar and a hydroxyl group of another sugar); and/or (2) the formation of a sugar anhydride bond, (e.g., the elimination of a water molecule between any hydroxyl group other than those involved in glycosidic bond formation). Any reaction condition or sequence that may result in these bond formations can be applied to this synthesis. Typically the hydroxyl group will be activated prior to oligomerization. Such conditions are known in the art. For example, an anomeric hydroxyl group can be transformed to a halogen functionality (such as Cl, Br, or I) when the sugar is treated with an appropriate transition metal salt such as $HgX_2$, or the halogen itself, such as $X_2$. This hydroxyl group can also be transformed into an activated ester-like functionality when treated with toluenesulfonyl or methanesulfonyl chloride. These resultant products from the above reactions can readily react with the hydroxyl functionalities of another sugar to give a glycosidic linkage. These transformations can also occur at the hydroxyl groups other than the one directly attached to the anomeric carbon, therefore leading to the formation of sugar anhydrides. Oligomerizing reactions, according to the present invention, are a particular type of the class of displacement reactions in which the displacing group is an alkoxide.

Often it is desirable that the reaction products be reduced. There are many sets of conditions known in the art for reduction, any of which may be used in the practice of the present invention. These include catalytic reduction using Raney-nickel, platinum, palladium, or platinum-carbon. Hydride reduction can also be used. Such reduction may employ $LiAlH_4$, $NaAlH_4$, and $KAlH_4$.

The multiple hydroxyl functionalities attached to the carbon-carbon backbones can be directly or indirectly transformed into other chemical moieties as desired. For instance, any of these hydroxyl groups can be displaced randomly by a simple halogen, thereby directly transforming the saccharide(s) into an array of halogenated saccharides. In addition, these hydroxyl groups may first be activated to sulfonated esters then displaced with either halogen, azide, nitrile, alkoxide, or sulfite, thereby indirectly transforming the saccharide(s) into an array of either halogenated, nitrogenated, sulfurized, and/or oligomerized saccharides.

The saccharide may also be transformed into other chemical moieties indirectly via oxidation of the hydroxyl functionalities. For example, the hydroxyl functionalities of saccharides can be oxidized to carbonyl functionalities randomly to give a family of partially oxidized sugars. These partially oxidized sugars can subsequently be transformed into other chemical functionalities based on the reactions of the carbonyls, thereby indirectly transforming the saccharides into an array of new chemical entities which may not resemble the starting material. Prior to oxidizing hydroxyl functionalities it is desirable to react the polyhydroxyl-containing organic compounds with subequimolar amounts of protecting groups. Protecting groups are those which are not sensitive to the oxidizing conditions used to transform the hydroxyl groups to carbonyl moieties.

A combination of such functional groups can be introduced directly or indirectly so that any number Of the original hydroxyl groups of a saccharide are displaced by other chemical moieties. The oligomerization and functionalization of polyhydroxyl compounds such as saccharides can be carried out sequentially or concurrently. The number of organic compounds present in each library, as a consequence of prior chemical events, will be multiplied by the next random chemical transformation to expand the collection of organic compounds.

According to the present invention it is desirable to minimize the differences among saccharidic hydroxyl groups during the reaction process, and thus force the formation of multiple reaction products. This is contrary to the conventional strategy in synthetic chemistry, where the purpose of the reaction is to form a particular product, and reaction specificity is the aim. However, the goal of this invention is to provide means to generate many reaction products, rather than to identify specific reaction conditions where a limited number of carbohydrate derivatives can be generated. According to the present invention differences among saccharidic hydroxyl groups are minimized by using small and highly reactive reagents to minimize the steric hindrance during the reaction process. Such reagents include methanesulfonyl chloride, toluenesulfonyl chloride, and halogen salts such as $PBr_5$, $PBr_3$, HBr, HI, and LiI. Other means for reducing reaction specificity include: (1) selectively blocking the reaction sites that are either more reactive than the others (such as the (C-1 anomeric hydroxyl groups) or sterically more accessible than the others (such as the C-6 hydroxyl group of a hexopyranoside); and/or (2) using sub-molar equivalent (subequimolar) amounts of chemical reagents in the transformation steps. Selective blocking can be accomplished by using protecting groups as are known in the art. For the hydroxyl groups on the anomeric carbon, such groups include $CH_3O^{31}$, and $C_2H_5O^{31}$, etc., which can be derived from the alkanols. For the stereochemically most accessible C-6 site of a hexose pyranoside, such as glucose pyranoside, such groups include trityl (triphenylmethyl), TPS (triphenylsilyl), TBMPS (t-butylmethoxyphenylsilyl), etc. Useful protecting groups are those which are not displaced by the displacing groups which are employed in the subsequent step.

In contrast to the combinatorial peptide and nucleotide libraries described to date which involve the sequence randomization of individual monomers using a single, naturally existing, biological linkage, the present invention employs a multiplicity of linkages between monomers, large numbers of sequences of linked monomers, and a multiplicity of different chemical transformation products. This invention makes use of highly functionalized polyhydroxylated compounds ("polyhydroxyl-containing organic compounds") to generate chemical libraries. The members of this collection will include the naturally existing biological linkages among other linkages.

Libraries which are generated can be screened for any biological activity known in the art. These include, but are not limited to, antimicrobial activity, antitumor activity, enzyme inhibiting activity, receptor binding, growth promotion activity, and in vitro and in vivo tests for biological responses. Many assays are known for these activities in the art and any can be used as is convenient.

Once a mixture or library has been found which contains a desired biological activity, fractionation of the mixture or library is desirable. Any fractionating means known in the art can be employed. Typically these will involve solvent partitioning and/or conventional chromatography, which may include liquid column chromatography, thin layer chromatography, high performance liquid chromatography, affinity chromatography, or ion exchange chromatography. Individual fractions can then be tested to locate the fraction with the desired biological activity. Fractionation can be repeated or combined with other fractionation steps and the fractions again tested for activity. In such a manner, the active ingredient can be isolated and purified from the highly complex mixture of reaction products.

In the following examples we demonstrate that: (1) a mixture of three common monosaccharides, through a sequence of chemical transformations, can be used to generate a mixture of aminoglycosides and their analogs, some of which are active against pathogens (FIG. 1a and Table 1, libraries #1 to #3a and #3b); and (2) the products of a single trisaccharide are active against infectious pathogens after a sequence of chemical transformations (FIG. 1b, c and Table 1, libraries #4–7c).

Figure 1:
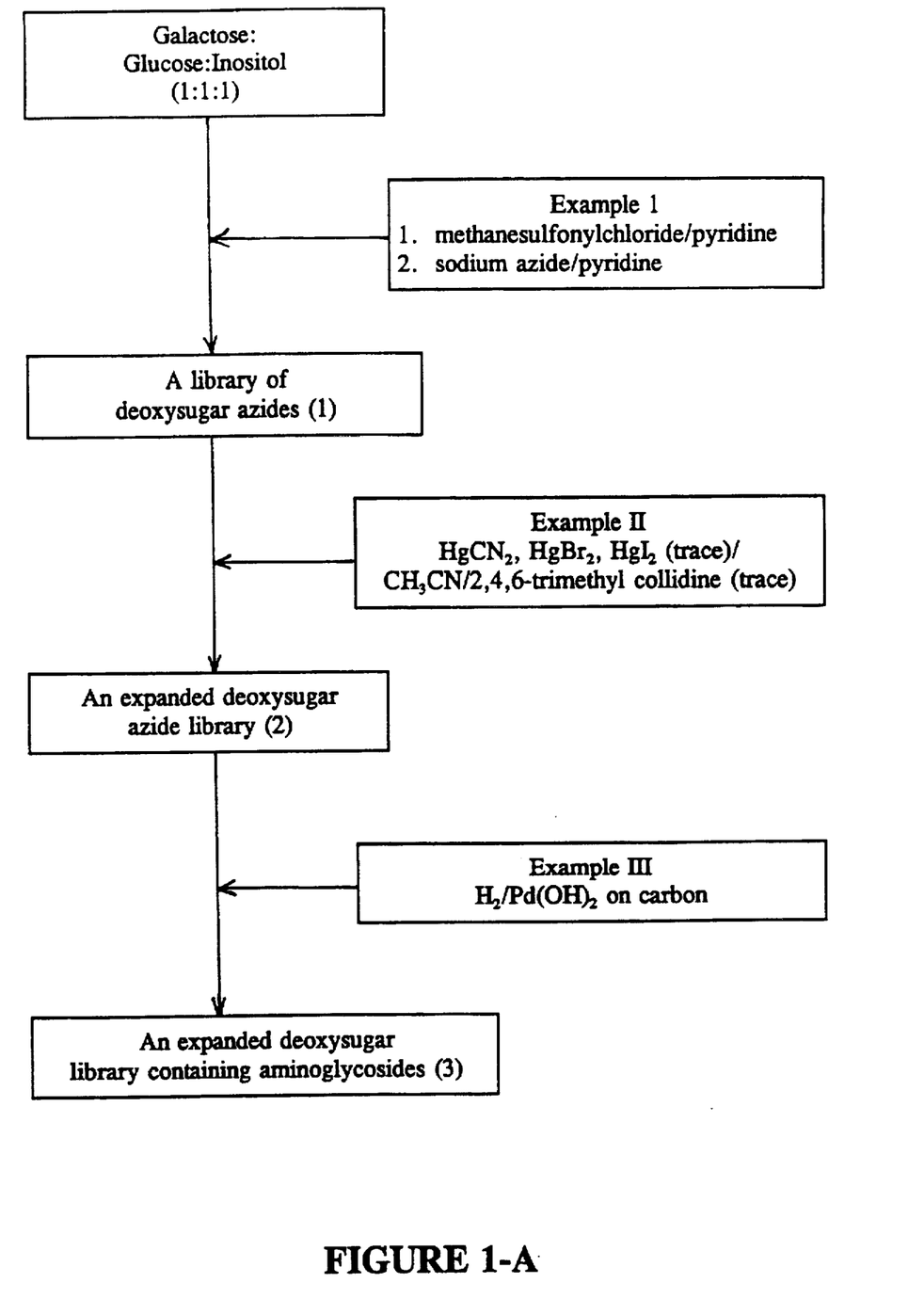
FIG. 1 represents three reaction schemes for generating a complex mixture of compounds using a mixture of simple saccharides or a single oligosaccharide as the basic starting materials.

FIG. 1 summarizes the synthetic schemes used to generate the compound libraries. Table 1 summarizes the antimicrobial assay results of these libraries against methicillin resistant *Staphylococcus aureus* (MRSA), *Bacillus subtilis* (*B. sub*), *Pseudomonas aeruginosa* (*Ps. aerug.*), *E. coli*, and *Candida albicans* (*C. alb.*). Synthetic methods are given in detail in the examples. The in vitro bacterial susceptibility tests were conducted according to the method specified in the 4th edition of *Manual of Clinical Microbiology* (Barry, A. L.; and Thornsberry, C. 1985. Ed. by Edwin H. Lennette (editor-in-chief). American Society for Microbiology, Washington, D.C.; pp. 978).

In Examples I–III depicted in FIG. 1, and described in more detail below, a sequence of chemical libraries was built, one upon the other, starting with three simple monosaccharides, namely glucose, galactose, and inositol (in 1:1:1 ratio). First, methanesulfonyl chloride was introduced to a mixture of the three monosaccharides under a basic condition (pyridine, a basic solvent). The resultant sulfonyl esters generated in situ activated the hydroxyl functionalities of the sugars. These activated ester moieties could be either displaced by the hydroxyl group of another sugar, which would produce either oligomeric glycosides or sugar anhydrides, or displaced by another nucleophilic group, such as azide. Due to the multiple hydroxyl functionalities of sugars, both chemical processes (i.e., the oligomerizations by other sugar displacements of the activated esters and the displacements by azide) could happen simultaneously. As a consequence of the randomized reactions, library #1 contained deoxy-azido-sugars in either oligomeric or monomeric forms. HPLC gel permeation analysis using TSK-1000 HXL indicated that there were nearly 14% dimers present in library #1.

The oligomerization reaction introduced here significantly increased the possible number of different oligomers present in library #2 by formation of different glycosidic linkages. A portion of library #1 was treated with $Hg(CN)_2$, $HgBr_2$ and $HgI_2$ in acetonitrile in the presence of base to increase the percentage of the oligomeric sugars, which led to the expanded library #2. This reaction step expanded the collection of different oligomers via the anomeric carbon (C-1) of the sugars. As indicated by the same gel permeation analysis, 27% dimers and trimers were found (indicating a 13% increase in the oligomers).

Following the library expansion reactions, the deoxy-azido-sugar library #2 was converted to the deoxy-amino-sugar library #3 via catalytic reduction using hydrogen and palladium oxide on carbon. This reaction did not appreciably increase the number of compounds present in the library; rather, it converted the compounds from azido- functionality to the corresponding amino- functionality. The resultant library #3 was partitioned between water and ethyl acetate to give library #3a, the aqueous fraction of library #3, and library #3b, the organic fraction of library #3.

Table 1 summarizes the antimicrobial activity profile of libraries #1, #2, #3a and #3b. Note that all of the libraries showed antimicrobial activity. The deoxy-azido sugar libraries #1 and #2 showed activity only against gram positive bacteria, *B. subtilis* and *Staphylococcus aureus*, whereas the deoxy-amino sugar library #3a showed activities against the same species of gram-positive bacteria as well as the gram-negative bacteria, *E. coli* and *Pseudomonas aeruginosa*. The organic fraction, library #3b, only showed activity against *B. subtilis*.

As discussed previously, one can establish a library of chemical compounds by randomly displacing the hydroxyl functionality with another chemical moiety, such as a nitrogen containing group. Examples IV–VII depicted in FIG. 1 used a single trisaccharide, raffinose[1], to prepare a sequence of libraries containing aminoglycosides.

[1]β-D-fructofuranosyl-O-α-D-galactopyranosyl-(1–6)-α-D-glucopyranoside

In Example IV, raffinose, which contains eleven free-hydroxyl groups, was first reacted with four molar equivalents of benzylchloroformate in pyridine. Introduction of the benzylformate protecting group ensured that an average of 4 molar equivalents of hydroxyl functionality were present in the subsequent amino-sugar libraries. Immediately following the random protecting steps, 7 molar equivalents of methanesulfonyl chloride were introduced to generate the activated esters in situ, which were then converted to a deoxy-azido-sugar library #4 by azide displacement.

The azide-library #4 was then converted to an amino-sugar library by catalytic reduction, and the benzylformate protecting groups were removed to produce the amino-sugar library #5. The resultant library #5 was partitioned between organic solvent and water to give libraries #5a, the aqueous fraction, and #5b, the organic fraction.

Libraries #4, #5a and #5b were tested against a battery of microbes. The results are shown in Table 1. Library #4 did not exhibit any antimicrobial activity, whereas library #5a showed activity against gram positive bacteria and #5b showed a limited activity against *E. coli*.

Examples VI and VII, which produced libraries #6, #7a, #7b, and #7c, started with the same starting material as libraries #4 and #5, and used the same reaction sequence to introduce nitrogen and generate amino-sugars. Examples VI and VII differ from IV and V in that different hydroxyl protecting groups were introduced. First, 2 molar equivalents of $CH_3I$ were introduced so that an average of two raffinose hydroxyl groups were converted to a methoxyl functionality. Following this reaction, 4 molar equivalents of benzyl group were introduced, so an average of 4 hydroxyl groups per molecule would not be converted or displaced by other chemical functionalities, and could be converted back to free hydroxyl upon catalytic reduction. These two consecutive alkylation steps led to the formation of library #6. As in all of the previous reaction schemes, library #6 was then converted to the deoxy-azido-sugar library #7a, followed by catalytic reduction and partition to give libraries #7b, the aqueous fraction, and #7c, the organic fraction.

The biological activities of libraries #6, #7a, #7b and #7c are indicated in Table 1. Libraries #6, #7a, and #7c did not exhibit any antimicrobial activity against the test organisms. Library #7b showed activity against *E. coli* and *Candida albicans*.

As demonstrated by these examples, different spectra of biological activities were obtained when the preparation of compound libraries started with different saccharides. As shown in Table 1, libraries #1–#3 exhibited a broader spectrum of biological activity against the battery of chosen microbes than did libraries #4–#7. The primary difference was that the preparation of compound libraries #1–#3 started with three different monosaccharides. The aminoglycoside library #3a exhibited a broad spectrum of antimicrobial activity against both gram positive and gram negative bacteria. On the other hand, the preparation of libraries #4–#7 started with a single trisaccharide to give a sequence of aminoglycoside libraries. These libraries exhibited different antimicrobial profiles, as indicated in Table 1.

Starting with the same material, different chemical libraries can be prepared with different biological activity profiles. As demonstrated in Table 1, the compound libraries #4–#5 and #6–#7 were all prepared with raffinose. These libraries differ in the means used to introduce the different hydroxyl protecting groups and the methylation of the aminoglycoside libraries. In the sequence which gave libraries #4–#5, a benzylformate protecting group was used, whereas the other libraries used a mixture of methyl and benzyl protecting groups. After the catalytic reduction, library #7b was randomly methylated whereas the library #5a was not. Library #7b exhibited anti-yeast (*C. albicans*) activity, whereas the library #5 exhibited antibacterial activity, as indicated in Table 1.

EXAMPLES

Example I.

Preparation Of A Saccharide Based Organic Compound Library #1

A mixture of glucose (2 g, 11.11 mM), galactose (2 g, 11.11 mM) and inositol (2 g, 11.11 mM) was suspended in freshly distilled (over $CaH_2$) pyridine (ca. 100 mL) and stirred at room temperature (25° C.) for 16 hrs under Ar. Methanesulfonyl chloride (14 mL, 5.34 Meq) was added to the reaction mixture dropwise under Ar while the reaction mixture was chilled with an ice bath. The reaction temperature was then gradually brought back to ambient temperature as the ice melted (approx. 45 min). The resultant solution was then stirred vigorously under Ar at ambient temperature for another 16 Hrs. The resultant pyridinium chloride precipitate was then removed via filtration with a double-end schlenck filter under reduced pressure and a positive flow of Ar. The filtrate was directly transferred over solid sodium azide (6.6 g, 3 Meq). The suspension was then stirred at ambient temperature for another 48 hrs under Ar. The reaction mixture was then frozen with liquid $N_2$, and left on the vacuum ( ca. 0.5–1 torr) until the pyridine was completely evaporated (ca. 16–24 hrs) to give a dark-brown colored amorphous solid. A mixture of distilled and deionized $H_2O$ and acetonitrile (70 mL: 100 mL) was added to the solid and the mixture was left to stand at room temperature for about 10 min. HCl (0.1%, aq, 200 uL) was then added to the solution, which immediately separated into two layers. The aqueous layer (bottom) was then separated from the organic layer (top) using a separatory funnel. The aqueous layer was then washed twice with acetonitrile (100 mL×2). The organic extract and washes were then combined and concentrated under vacuum with rotary-evaporator and vacuum (0.5 to 1 torr) to give a brown-colored amorphous solid as the crude mixture of library #1 (19.65 grams). The aqueous layer was freeze-dried to give a crude solid. The proton NMR analysis indicated that this fraction is the pyridinium methanesulfonate salt. The successful displacement is first indicated by the changing of the carbohydrate solubility from polar protic solvent ($H_2O$) to polar aprotic solvent ($CH_3CN$). The LC and HPLC gel permeation (TSK 1000 HXL/THF) analysis indicated that approximately 14% of the crude mixture were the products of dimerization (M.W.>400). The presence of the multiple $N_3$ on the carbohydrate skeletons and their different locations is indicated by the same analysis. Their different substitution location on the carbohydrate skeletons can also be observed. The presence of the proton signal from aldehydes rather than from the anomeric carbon is due to the azide displacement at the C-4 and C-5 position of the carbohydrate skeleton. This displacement trapped the sugars in their aldehyde form rather than their common pyranoside and furanoside form. The mixture was then tested for in vitro antimicrobial activities using the impregnated disc-assay. The biological activity test results of library #1 are given in Table 1.

Example II.

Expansion of the Saccharide Library #1 to Library #2

A portion of the crude library #1 (4.97 g) was dissolved in $CH_3CN$ (ca. 250 mL, dried with 4 A molecular sieves). The solution was stirred under Ar on an ice bath for 15 min. 2,4,6-trimethyl collidine (1 mL), $Hg(CN)_2$ (0.97 g), $HgBr_2$ (2.67 g), and $HgI_2$ (0.45 g) was added to the above solution sequentially. The reaction mixture was then stirred at room temperature for 20 hrs and poured over a suspension of ethyl acetate (200 mL) over saturated sodium bicarbonate solution (150 mL). The layers were then separated, and the organic layer was washed with additional aqueous base (3×150 mL). The aqueous washes were combined and extracted once more with ethyl acetate (200 mL×1). The organic layers were combined and concentrated to complete dryness to give a yellow colored amorphous solid. A portion of the solid (630 mg) was then dissolved in a mixture of $C_2H_5OH$ and $CH_3CN$ (3 mL; 1:1, v: v) and loaded onto a gel permeation column (LH-20, 2.8 cm×90 cm, packed in $CH_5OH/CH_3CN$, 1:1 v:v). The column was then developed with $C_2H_5OH/CH_3CN$ (50:50) in which the crude product was dissolved. A total of 11 fractions (ca. 75 ml each) were collected. The sugar-containing fractions (frac. 2–6) indicated by NMR analysis were combined and the solvents were removed by vacuum to give library #2, a light yellow colored solid (376.8 mg, ca. 60% of the crude mixture). The HPLC gel permeation analysis of the crude mixture indicated that the percentage of the oligomerization product with molecular weight about 400 increased from 14% to 27%. The biological activity profiles of the library #2 is shown in Table 1.

Example III.

Conversion of the Saccharide Library #2 to a Library Containing Aminoglycosides (Library #3)

In a jacketed hydrogenation tube, ca. 180 mg of library #2 was dissolved in $CH_3OH$ (3 mL) with a suspension of palladium hydroxide on carbon (270 mg). A positive pressure of $H_2$ was added (approx 5 to 7 psi) while the tube was mixed vigorously. The reduction process was carried out for 16 hr at ambient temperature. The resultant slurry was then filtered, and the catalyst was sequentially washed with THF, $CH_3OH$, and water. All of the filtrates were combined and concentrated to dryness to give a colorless glass-like solid. A reverse phase thin layer chromatography analysis using C18 (developed with 25% MeOH in $H_2O$) indicated the presence of $NH_x$ ($NH_x$=the primary amino $NH_2$and secondary amino $NH_1$ hereafter) by the color development of ninhydrin spray. The solid was then partitioned in ethyl acetate and $H_2O$ (50 mL 1:1, v:v) and the organic layer was separated from the aqueous layer. Both layers were concentrated to dryness. The aqueous layer gave a glassy oil slurry (library #3a, 59.5 mg), whereas the organic layer gave a white colored solid (library #3b, 85.7 mg). A portion (10 uL) of the aqueous layer was taken, and spotted onto a silica gel plate (without developing with solvent), spraying with 1% ninhydrin (in $CH_3OH$ with trace amount of acetic acid) indicated the presence of $NH_x$ functions. The organic portion, which only had a very faint ninhydrin-color-analysis, was analyzed by gel permeation. The biological activities of both library #3a and #3b are shown in Table 1.

Example IV.

Preparation of a Saccharide Library Based on a Single Carbohydrate (Library #4)

Raffinose pentahydrate (500mg 0.84 mM) was dissolved in 18 mL of freshly distilled (over $CaH_2$) pyridine and cooled with an ice bath (5°–10° C.) under Ar. Benzylchloroformate (0.4 mL) was then added dropwise to the solution while the solution was vigorously stirred under Ar at 0° to 5° C. (ice/water slurry-bath temperature). The reaction was then continued with stirring under the above conditions for about 30 min., at which time methanesulfonyl chloride (0.4 mL) and another portion of benzylchloroformate were added. The reaction mixture was then stirred under the above conditions for another 30 min. followed with the addition of an additional portion of methanesulfonyl chloride (0.4 mL). The entire reaction mixture was gradually warmed up to ambient temperature over 45 mins. and then allowed to stir under Ar for another 16 hrs. The pyridinium salt precipitate was then removed by filtration (with a double-end filter), and the filtrate was directly transferred into a flask containing $NaN_3$ (600 mg). The reaction mixture was then stirred at room temperature under Ar for 72 hr. The solvent was removed by vacuum (freeze dried over night); the resultant solid was partitioned between 100 mL of 10% MeOH in ethyl acetate (v:v) and water (eq. vol). The organic layer was then washed with HCl (0.1% conc. HCl in water; v:v; X2), saturated $NaHCO_3$ (eq. vol; X3) and saturated NaCl (eq. vol.; X1). The crude product was then concentrated to complete dryness to give an oily solid (library #4; 1.41 grams). The biological activity of library #4 is given in Table 1.

Example V.

Conversion of the Saccharide Library #4 to a Library Containing Aminoglycosides (Library #5)

A portion of Library #4 (ca. 700 mg) was suspended in a mixture of organic solvents (ethylacetate and methanol, 1:1, v;v; 50 mL), to which a catalytic amount of palladium oxide on carbon (50 mg) was added. The solution was then purged with hydrogen for 4 hrs with vigorous stirring at ambient temperature. The reaction vessel was sealed under a positive pressure of hydrogen (2–5 psi) and stirred at ambient temperature overnight. The reaction slurry was then filtered, and the catalyst washed with ethyl acetate, methanol and water. All filtrates and washes were combined and concentrated to dryness to give a white amorphous solid. The solid was then partitioned between ethyl acetate (20 mL) and water (20 mL), and the layers were separated from each other with a separatory funnel. The layers were concentrated to dryness. A ninhydrin color test indicated that both fractions contained $NH_x$'s. The results of the biological assays of the aqueous fraction, library #5a, and organic fraction, library #5b, are given in Table 1.

Example VI.

Construction of a Saccharide Library #6 from a Single Carbohydrate.

Raffinose pentahydrate (2 grams), NaH, (2 grams) and a trace amount of tetrabutylammonium iodide (50 mg) were added to DMF (dried over 4 A molecular sieve), while the reaction mixture was stirred under Ar over an ice bath. $CH_3I$ (430 uL; ca. 2 meq) was added dropwise to the reaction mixture. The mixture was then stirred under the above conditions for 35 min followed with an addition of benzylbromide (1.62 mL, 4 meq) dropwise. The reaction temperature was gradually raised to room temperature over 35 to 45 mins. The mixture was then stirred at the ambient temperature for another 20 hrs before lyophilization (another 48 hrs). The resultant oily solid (light tan colored) was suspended in a methanol/water (50/50, v:v) solution, and freeze-dried again to force a complete removal of the solvent. The dried solid was suspended in denatured ethanol (100 mL) and the insoluble residue was filtered to give a clear filtrate. The filtrate was then concentrated to dryness (9.0 grams). Analysis by reverse phase thin layer chromatography and NMR spectroscopy indicated the formation of multiple sugar-containing products. The crude mixture was then loaded onto a Toyopearl 40F gel permeation column and eluted with 5% (v:v) methanol in water. Sugar positive fractions were then combined to give a light yellow colored oily mixture of sugars (library #6; 3.45 gram, 38% of the crude). NMR analysis indicated the existence of multiple OMe (singlets from 2.50 to 3.20 ppm) attached to the sugar moiety. The results of the biological assays of library #6 are given in Table 1.

Example VII.

Conversion of the Saccharide Library #6 to a Library #7 Containing Aminosugars

An aliquot of library #6 (3 grams, crude) was dissolved in 50 mL of freshly distilled pyridine (50 mL) and cooled to 0°–5° C. with an ice bath. Methanesulfonyl chloride (ca. 1 mL) was then added dropwise for about 80 min. The reaction temperature was then gradually increased to room temperature (over 35 to 45 mins.) and the mixture was then stirred under Ar for an additional 3 hrs. The resultant slurry was filtered with a double-end filter under reduced pressure with a positive flow of Ar. The filtrate was directly added to a mixture of $NaN_3$ (2.6 gram) and crown ether (catalytic amount 600 mg). The solution was then stirred vigorously under Ar at ambient temperature for 16 hrs. The reaction temperature was brought to 50° C. with an oil-bath under Ar for 2 additional hrs, and cooled to the ambient temperature before filtration. The filtrate was then freeze-dried to remove the pyridine. The resulting oily solid was suspended in a mixture of solvents ($H_2O$, 3 mL; MeOH, 20 mL; and EtOAc, 10 mL). The milky suspension was loaded onto Toyopearl 40F column which was then eluted with EtOAc (100%). The fractions containing the OBz (broad multiplets at 7.1 to 7.5 ppm, C6H5) and OMe (multiplets at 2.6 to 2.8 ppm) signals by proton NMR analysis were combined and concentrated to dryness (library #7a, 450 mg). The NMR analysis also indicated the existence of the $CH-N_3$ functional groups by the broad multiplets at the 2.8 to 3.4 ppm. The biological testing result of library #7a is shown in Table 1.

Library #7a was then suspended in a mixture of solvents (20 mL, $CH_3OH$/EtOAc, 50:50, v:v) in the presence of a catalytic amount of Palladium oxide on carbon (50 mg). The reaction vessel was then purged with a positive flow of hydrogen with vigorous stirring for 5 hrs. The reaction vessel was then sealed while connected to a hydrogen tank with a hydrogen pressure at 2.5 psi. and the pressure was gradually raised to 15 psi during the next 72 hrs. The reaction mixture was then filtered, and the catalyst was washed sequentially with $H_2O$, MeOH and EtOAc. All washes and filtrates were combined and concentrated to dryness to give a pale white solid. The solid was then partitioned between 250 mL of water and 250 mL of EtOAc. The layers was then separated. The organic layer was washed once again with water, while the aqueous layer was washed once with EtOAc. The washes were then combined with the corresponding layers of extracts and solutions were then concentrated to dryness. The aqueous fraction gave a clear oily solid (library #7b, 194 mg) whereas the organic layer gave a light yellow colored solid (library #7c, 176 mg). The biological activity test results of the libraries #7b and 7c are given in Table 1.

TABLE 1

| | Antimicrobial Profiles of different saccharide libraries | | | | |
|---|---|---|---|---|---|
| Libraries | B. Sub. | MRSA* | E. coli | Ps. aerug | C. alb |
| 1 | + | + | − | − | − |
| 2 | + | + | − | − | − |
| 3a | + | + | + | + | − |
| 3b | + | − | − | − | − |
| 4 | − | − | − | − | − |
| 5a | + | + | − | − | − |
| 5b | − | − | ± | − | − |
| 6 | − | − | − | − | − |
| 71 | − | − | − | − | − |
| 7b | − | − | ± | − | + |
| 7c | − | − | − | − | − |

We claim:

1. A method for generating and screening a library of compounds, comprising:

reacting one or more polyhydroxyl-containing organic compounds with subequimolar amounts of displacing groups to form a first mixture comprising displacing group-substituted polyhydroxyl-containing organic compounds;

testing said first mixture or a reaction product made therefrom for the presence of a component displacing group-substituted polyhydroxyl-containing organic compound in said first mixture or said reaction product having a biological activity;

fractionating said mixture or reaction product which demonstrates biological activity to form fractions;

testing said fractions for said biological activity.

2. The method of claim 1 further comprising the step of:

oligomerizing a portion of said first mixture to form a second mixture comprising displacing group-substituted polyhydroxyl-containing organic oligomers.

3. The method of claim 1 further comprising the step of:

reducing a portion of said first mixture comprising displacing group-substituted polyhydroxyl-containing organic compounds using catalytic reduction or hydride reduction, to form a second mixture comprising displacing group-substituted, reduced polyhydroxya)—containing organic compounds.

4. The method of claim 1 further comprising the steps of:

oligomerizing a portion of said first mixture to form a second mixture comprising displacing group-substituted polyhydroxyl-containing organic oligomers;

reducing a portion of said second mixture comprising displacing group-substituted polyhydroxyl-containing organic oligomers to form a third mixture comprising displacing group-substituted, reduced polyhydroxyl-containing organic oligomers.

5. The method of claim 1 further comprising the step of:

alkylating a portion of said first mixture.

6. The method of claim 2 further comprising the step of:

alkylating a portion of said first or second mixtures.

7. The method of claim 3 further comprising the step of:

alkylating a portion of said first or second mixtures.

8. The method of claim 4 further comprising the step of:

alkylating a portion of said first or second or third mixtures.

9. The method of claim 1 further comprising the step of:

halogenating a portion of said first mixture.

10. The method of claim 2 further comprising the step of:

halogenating a portion of said first or second mixtures.

11. The method of claim 3 further comprising the step of:

halogenating a portion of said first or second mixtures.

12. The method of claim 4 further comprising the step of:

halogenating a portion of said first or second or third mixtures.

13. The method of claim 1 wherein hydroxyl groups on said polyhydroxyl-containing organic compounds are activated prior to reaction with displacing groups to form organic compounds containing activated hydroxyl functionalities.

14. The method of claim 13 wherein said activation is accomplished by reaction of said polyhydroxyl-containing organic compounds with a bromine or iodine salt.

15. The method of claim 13 wherein said activation is accomplished by reaction of said polyhydroxyl-containing organic compounds with methanesulfonyl chloride.

16. The method of claim 13 wherein said activation is accomplished by reaction of said polyhydroxyl-containing organic compounds with alkylsulfonyl chloride.

17. The method of claim 13 wherein said activated hydroxyl functionalities of said compounds are sulfonyl esters.

18. The method of claim 2 wherein said hydroxyl groups on said polyhydroxyl-containing organic compounds are activated prior to said step of oligomerizing.

19. The method of claim 18 wherein said activation is accomplished by reacting said polyhydroxyl-containing organic compounds with a sulfonyl compound.

20. The method of claim 18 wherein said activation is accomplished by reacting said polyhydroxyl-containing organic compounds with a halide compound.

21. The method of claim 18 wherein said activation is accomplished by reacting said polyhydroxyl-containing organic compounds with a thiolate compound.

22. The method of claim 13 or 18 wherein the amount of activated hydroxyl functionalities formed is controlled by first reacting said polyhydroxyl-containing organic compounds with subequimolar amounts of protecting groups.

23. The method of claim 1 wherein said steps of fractionating and testing are repeated until an active ingredient has been purified.

24. The method of claim 1 wherein the displacing group is a carbanion.

25. The method of claim 1 wherein the displacing group is a halogen ion.

26. The method of claim 1 wherein the displacing group is an azide ion.

27. The method of claim 1 wherein the displacing group is a nitrile.

28. The method of claim 1 wherein the displacing group is a sulfite.

29. The method of claim 1 wherein the displacing group is a thiolate.

30. The method of claim 1 wherein the displacing group is an alkoxide.

31. The method of claim 1 wherein a mixture of displacing groups is used in said step of reacting.

32. A method for generating and screening a library of compounds, comprising:

reacting one or more polyhydroxyl-containing organic compounds with subequimolar amounts of protecting groups to form a first mixture of randomly protected polyhydroxyl-containing organic compounds;

oxidizing said first mixture to form a second mixture comprising carbonyl-containing organic compounds;

testing said first or said second mixtures or a reaction product made therefrom for the presence of a component randomly protected polyhydroxyl-containing organic compound or carbonyl-containing organic compound having a biological activity;

fractionating said first or second mixture or a reaction product made therefrom which demonstrates biological activity to form fractions;

testing said fractions for said biological activity.

33. The method of claim 32 wherein said carbonyl-containing organic compounds are reacted with carbanions to form branched-chain, organic oligomers.

34. The method of claim 32 wherein said carbonyl-containing organic compounds are reacted with a Wittig reagent.

35. The method of claim 1 further comprising the step of:

oxidizing a portion of said first mixture to form a second mixture comprising carbonyl-containing organic compounds.

36. The method of claim 2 further comprising the step of:

oxidizing a portion of said first or second mixture to form a third mixture comprising carbonyl-containing organic compounds.

37. The method of claim 3 further comprising the step of:

oxidizing a portion of said first or second mixture to form a third mixture comprising carbonyl-containing organic compounds.

38. The method of claim 4 further comprising the step of:

oxidizing a portion of said first or second or third mixture to form a fourth mixture comprising carbonyl-containing organic compounds.

39. The method of claim 35 or claim 36 or claim 37 or claim 38, further comprising the step of:

reacting one or more polyhydroxyl-containing organic compounds with subequimolar amounts of protecting groups to form a mixture of randomly protected polyhydroxyl-containing organic compounds, prior to the step of oxidizing.

40. The method of claim 1 wherein the one or more polyhydroxyl-containing organic compounds are carbohydrates.

41. The method of claim 1 wherein the one or more polyhydroxyl-containing organic compounds are polyalcohols.

42. The method of claim 1 wherein the one or more polyhydroxyl-containing organic compounds are saccharides.

43. The method of claim 1 wherein the one or more polyhydroxyl-containing organic compounds are glycopeptides.

44. The method of claim 1 wherein the one or more polyhydroxyl-containing organic compounds are glycolipids.

45. The method of claim 1 wherein the one or more polyhydroxyl-containing organic compounds are monomeric acyclic compounds.

46. The method of claim 1 wherein the one or more polyhydroxyl-containing organic compounds are monomeric cyclic compounds.

47. The method of claim 1 wherein the one or more polyhydroxyl-containing organic compounds are polymeric cyclic compounds.

48. The method of claim 32 wherein the one or more polyhydroxyl-containing organic compounds are carbohydrates.

49. The method of claim 32 wherein the one or more polyhydroxyl-containing organic compounds are polyalcohols.

50. The method of claim 32 wherein the one or more polyhydroxyl-containing organic compounds are saccharides.

51. The method of claim 32 wherein the one or more polyhydroxyl-containing organic compounds are glycopeptides.

52. The method of claim 32 wherein the one or more polyhydroxyl-containing organic compounds are glycolipids.

53. The method of claim 32 wherein the one or more polyhydroxyl-containing organic compounds are monomeric acyclic compounds.

54. The method of claim 32 wherein the one or more polyhydroxyl-containing organic compounds are monomeric cyclic compounds.

55. The method of claim 32 wherein the one or more polyhydroxyl-containing organic compounds are polymeric cyclic compounds.

56. The method of claim 32 wherein the one or more polyhydroxyl-containing organic compounds are phenolics.

57. The method of claim 32 wherein the one or more polyhydroxyl-containing organic compounds are polyphenolics.

58. The method of claim 1 wherein the one or more polyhydroxyl-containing organic compounds are phenolics.

59. The method of claim 1 wherein the one or more polyhydroxyl-containing organic compounds are polyphenolics.

* * * * *